United States Patent
Nicola (12)

(10) Patent No.: US 6,383,772 B1
(45) Date of Patent: May 7, 2002

(54) ENZYMATIC CONVERSION IN A SOLVENT MIXTURE CONTAINING WATER AND FLOURINATED, NON-CHLORINATED SOLVENT

(75) Inventor: Mazin Nicola, Worthing (GB)

(73) Assignee: Advanced Phytonic Limited, West Yorkshire (GB)

( * ) Notice: Subject to any disclaimer, the term of this patent is extended or adjusted under 35 U.S.C. 154(b) by 0 days.

(21) Appl. No.: 09/486,691

(22) PCT Filed: Sep. 3, 1998

(86) PCT No.: PCT/GB98/02645

§ 371 Date: Mar. 2, 2000

§ 102(e) Date: Mar. 2, 2000

(87) PCT Pub. No.: WO99/13098

PCT Pub. Date: Mar. 18, 1999

(30) Foreign Application Priority Data

Sep. 5, 1997 (GB) ............................................. 9718740

(51) Int. Cl.$^7$ .......................... C12P 37/06; C12P 37/00; C12P 1/00; C12P 35/02
(52) U.S. Cl. ............................ 435/44; 435/43; 435/51; 435/41
(58) Field of Search ............................. 435/44, 43, 51, 435/41

(56) References Cited

U.S. PATENT DOCUMENTS

| 3,530,148 A | 9/1970 | Miyake et al. ............... 549/353 |
| 5,500,352 A | 3/1996 | López .......................... 435/44 |

FOREIGN PATENT DOCUMENTS

| DE | 19 07 365 | 9/1969 |
| EP | 0 122 681 | 10/1984 |
| EP | 0 138 338 | 4/1985 |
| EP | 0 496 993 | 8/1992 |
| WO | 82 01563 | 5/1982 |
| WO | 97 35029 | 9/1997 |

OTHER PUBLICATIONS

Mori et al, "Transglycosylation in a Two–Phase Aqueous–Organic System with Catalysts by a Lipid–Coated Beta–D–Galactosidase", Carbohydrate Research, vol. 298, No. 1/02, Feb. 20, 1997, pp. 65–73.

Martinek et al, "Enzymatic synthesis in biphasic aqueous–organic systems", Biochimica Biophysica Acta, vol. 658, 1981, pp. 76–89.

Legoy, "The Kinetic behavior of a two–enzyme system in biphasic media: coupling hydrolysis . . . ", Biochimica Biophysica Acta, vol. 1337, No. 2, Feb. 8, 1997, pp. 227–232.

Andersson et al., "Bioconversion in aqueous two–phase system", Enzyme Microb. Technol., vol. 12, Apr. 1990, pp. 242–254.

Baldaro et al., "Phenylacetyloxymethylene, a carboxyl protecting group removable with immobilized penicillin amylase . . . ", Tetrahedron Letters, vol. 29, No. 36, 1988, pp. 4623–2634.

Guisan et al., "Industrial design of enzymatic processes catalyzed by very active immobilized derivatives . . . ", Biotechnol. Appl. Biochem., vol. 20, No. 3, Dec. 1994, pp. 357–369.

*Primary Examiner*—David M. Naff
*Assistant Examiner*—Mike Meller
(74) *Attorney, Agent, or Firm*—Arent Fox Kintner Plotkin & Kahn, PLLC

(57) ABSTRACT

A first compound is converted to a second compound enzymatically in a solvent mixture containing water and a fluorinated, non-chlorinated alkane, alkene, or alkyne having up to 4 carbon atoms. Lactams, for example 6-aminopenicillanic acid (6-APA), may be prepared by enzymatic conversion of a first compound, for example penicillin-G, in a solvent mixture comprising water and a non-aqueous organic solvent, for example 1,1,1,2-tetrafluoroethane. The 6-APA can be caused to precipitate, isolated by filtration and optionally derivatized to produce a desired compound. A by-product of the enzymatic conversion, for example phenylacetic acid, can be isolated by solvent extraction, suitably using a solvent which also comprises 1, 1, 1, 2-tetrafluoroethane.

23 Claims, No Drawings

ENZYMATIC CONVERSION IN A SOLVENT MIXTURE CONTAINING WATER AND FLOURINATED, NON-CHLORINATED SOLVENT

BACKGROUND OF THE INVENTION

DESCRIPTION OF THE RELATED ART

This invention relates to the preparation of a compound, especially an active pharmaceutical compound. Particularly, although not exclusively, the invention relates to the preparation of lactams, for example penicillins and cephalosporins and/or derivatives thereof.

6-Aminopenicillanic acid (6-APA) and 7-aminodesacetoxycephalosporanic acid (7-ADCA) are intermediates used for the manufacture of most semi-synthetic β-lactam antibiotics. The commercially preferred method for the manufacture of 6-APA is by means of biochemical de-acylation of benzyl penicillin, commonly known as Pen-G or equivalent enzymatic deacylation of phenoxymethyl penicillin, commonly known as Pen-V. This is achieved using an enzyme such as penicillin acylase, which has been immobilised on an insoluble matrix such as polystyrene or polyacrylate polymers or co-polymers.

Various processes using this technique are illustrated in the scientific literature. In such processes, penicillin-G is isolated from a fermentation liquor as a solid intermediate using known means and is then dissolved in water in a relatively dilute solution (e.g. 5% w/v). The enzymation reaction (shown in scheme 1 below where R represents a potassium or sodium ion) is carried out at an elevated temperature (e.g. 35–40° C.). Phenylacetic acid (PAA) produced is neutralised by the continuous addition of dilute aqueous sodium hydroxide (e.g. 5% w/v) to maintain a pH of around 8.0. The isolation of 6-APA is normally carried out by concentration of the enzymation reaction liquors to, for example, 15% with respect of 6-APA in order to maximise yield, followed by precipitation with a dilute inorganic acid, such as 5% nitric acid or sulphuric acid. The PAA is removed by extraction into an immiscible organic solvent, such as methyl iso-butylketone or butyl acetate. The 6-APA is finally removed by filtration, washed with acetone then dried under vacuum. An acceptable standard conversion yield for the de-acylation process described is 94–96% and is 82–86% for the precipitation and isolation stage.

SCHEME 1

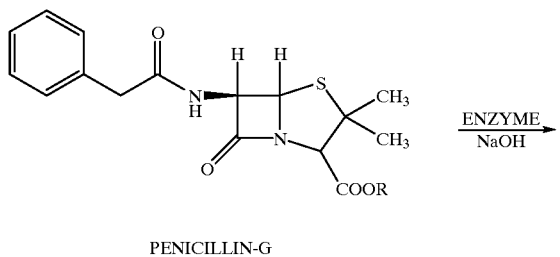

PENICILLIN-G

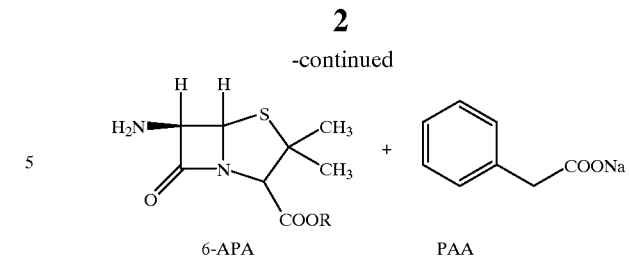

6-APA       PAA

The immobilised enzymes used in the above described process may be sensitive to product inhibition. Hence, the reaction is normally carried out on relatively dilute solutions. A drawback of this is that the solubility of 6-APA in water is around 2% which means that a concentration step is necessary in order to minimise product losses in the mother liquors. A costly concentration step is therefore often applied to increase 6-APA content to 12–16%.

PAA constitutes one of the ingredients normally used in the fermentation of penicillin-G. It is therefore, commercially advantageous to recover PAA from the reaction effluent so that it can be recycled. Conventional methods used commercially for the recovery of PAA employ a multistage process involving a combination of two or more of the following techniques: Vacuum distillation, purification (e.g. carbon treatment), extraction into an aqueous phase, chromatography, precipitation, filtration and drying. These techniques are relatively expensive and environmentally problematical.

It is the object of this invention to address the problems described above.

SUMMARY OF THE INVENTION

A method of preparing a second compound by catalytic conversion of a first compound, the method comprising contacting said first compound and a catalyst in a solvent mixture comprising water and a first non-aqueous solvent and wherein said catalyst is an enzyme.

DETAILED DESCRIPTION OF THE INVENTION

According to a first aspect of the invention, there is provided a method of preparing a second compound by a catalytic conversion of a first compound, the method comprising contacting said first compound and a catalyst in a solvent mixture comprising water and a first non-aqueous solvent.

Unless stated otherwise, or the context otherwise requires, a reference to any compound herein includes a reference to a salt of the compound.

Said catalyst is preferably an enzyme. Said enzyme may be sensitive to said second compound, for example in the sense that relatively high concentrations of said second compound may reduce the ability of the enzyme to effect the conversions—an effect know as "product inhibition".

Said enzyme is preferably capable of catalysing a deacylation reaction. It may suitably comprise an acylase which may be produced from any penicillin acylase producing micro-organism such as Escherichia, especially *Escherichia Coli*, Pseudomonas, Streptomyces, Proteus and Micrococus. Said enzyme is preferably immobilised, suitably by physical absorption or bonding to a solid, insoluble matrix.

Said first compound is preferably of general formula $R^1NHQ$ wherein $R^1$ represents an optionally substituted alkylcarbonyl group and Q represents an optionally substituted cyclic group, especially an optionally substituted lactam, for example a β-lactam group.

Unless stated otherwise, an optionally substituted alkyl group may have up to 12, preferably up to 8, more preferably up to 6, especially up to 4 carbon atoms. Optional substituents of a said alkyl group include optionally substituted aryl, alkenyl, alkynyl, acyl, nitro, cyano, alkoxy, hydroxy, amino, alkylamino, sulphinyl, alkylsulphinyl, sulphonyl, alkylsulphonyl, sulphonate, amido, alkylamido, alkoxycarbonyl, halocarbonyl and haloalkyl groups and halogen, especially fluorine, chlorine or bromine atoms.

Preferred optional substituents of said alkylcarbonyl group include optionally substituted, especially unsubstituted, phenyl, carboxy and amino groups.

In preferred embodiments, said group $R^1$ may be a optionally-substituted benzylcarbonyl group or a group C(COOH) (NH$_2$) HCH$_2$CH$_2$CH$_2$C (O)—or a salt thereof.

Said group Q may comprise a lactam fused to another optionally-substituted cyclic moiety which may be a 5- or 6-membered ring.

Said first compound may be a natural product, especially a product of a fermentation reaction or a derivative thereof. Said first compound is preferably an antibiotic. The method of the first aspect may include the step of preparing said first compound by a biochemical, especially a fermentation, process.

The ratio of the weight of said first solvent to that of water in said solvent mixture may be at least 2, preferably at least 5, more preferably at least 7, especially at least 10. In some cases, it may be at least 15 or 20. Said ratio may be less than 100, preferably less than 50, more preferably less than 30, especially 20 or less. The ratio referred to is suitably present at any time during the conversion reaction but preferably refers to the ratio at the start of the reaction.

The ratio, as % w/v, of said first compound to the water present in said mixture may be at least 10, suitably at least 20, preferably at least 30, more preferably at least 40, especially 50 or more. The ratio may be less than 100, suitably less than 90, preferably 80 or less. The ratio referred to is suitably present at any time during the conversion reaction but preferably refers to the ratio at the start of the reaction.

Said first non-aqueous solvent may have a boiling point, at atmospheric pressure, of less than 80° C., suitably less than 60° C., preferably less than 40° C., more preferably less than 20° C. Especially preferred solvents have a boiling point of less than 0° C., preferably less than −10° C. The boiling point may be greater than −90° C., preferably greater than −70° C., more preferably greater than −50° C.

Said first solvent is preferably organic. It may be aromatic, but is preferably aliphatic. It may include less than 10, suitably less than 8, preferably less than 6, more preferably less than 4, especially 2 or fewer carbon atoms. It may be an optionally-substituted alkane, alkene or alkyne. $C_{1-4}$ optionally-substituted alkanes are preferred. It is preferably halogenated. It may include less than 10, suitably less than 8, preferably less than 6, more preferably less than 5, especially 4 or fewer halogen atoms. Preferred halogen atoms include fluorine, chlorine and bromine atoms, with fluorine and chlorine atoms being preferred and fluorine atoms being especially preferred.

Preferably, said first solvent is non-chlorinated. It preferably comprises one or more carbon, fluorine and hydrogen atoms only.

Preferably, said first solvent is tetrafluoroethane, with 1,1,1,2-tetrafluoroethane being especially preferred.

Said solvent mixture may include other solvents.

Said second compound particularly when in free acid form (i.e. when not a salt), may be at least 0.1%, suitably at least 0.5%, preferably at least 1.0%, more preferably at least 1.5%, especially about 2% soluble in water. The aforementioned solubilities are preferably measured at 5° C.

Said second compound in salt form, for example as an alkali metal salt, may have a solubility in water of at least 5% w/v, preferably at least 10% w/v, more preferably at least 15% w/v.

The method preferably includes the step of adjusting the pH of the reaction mixture during the conversion reaction, suitably to maintain it within a physiologically-acceptable pH range. The pH is preferably in the range 7 to 9, more preferably in the range 7.8 to 8.2.

In a first embodiment, the method may include isolating the second compound from other compounds/solvents. Isolation may include causing the precipitation of the second compound and subsequent isolation of the precipitate by filtration. Precipitation may be caused by adjusting the pH at or close to the PKa value of the said second compound. Suitable pH may be less than 5, preferably less than 4. Suitable pH may be above 2.5, preferably above 3.5. Suitably a substantially insoluble form of the second compound is produced. The pH may conveniently be adjusted by the addition of an aqueous solution of an acid such as 1M or 2M nitric acid or preferably 1M or 2M sulphuric acid. The filtered said second compound may be washed with a second solvent. Traces of the second solvent may be substantially or wholly removed from the filtered product by evaporation.

In a second embodiment of the invention, the method may include adjusting the pH in the presence of a second solvent to a value at which the said second compound is substantially soluble in the aqueous phase of the solvent mixture whilst the by-products of the reaction are substantially soluble in the immiscible said second solvent phase of the solvent mixture. Suitable pH may be less than 2.5, more suitably less than 2. The pH may suitably be 1 or above. The solution of the said second solvent may be separated from the aqueous phase containing said second compound by settling and physical separation, thereby yielding an aqueous reaction liquor containing said second compound. The said reaction liquor may be washed with a quantity of the said second solvent in order to remove contaminant traces of the reaction by-products. The said second compound may be precipitated from said reaction liquor by adjusting the pH with a suitable base to produce a substantially insoluble form of said second compound. A suitable base may be an aqueous solution of sodium hydroxide, potassium hydroxide or ammonia. The pH may suitably be adjusted to above 2.5, more suitably to above 3.5. The pH may suitably be below 5, preferably below 4. Yield of said second compound is both said first or second embodiments may be maximised by stirring at reduced temperature, preferably between 2 and 10° C. Said second compound may be isolated by filtration, washing and drying.

Said second solvent used in the first and second embodiments described preferably includes said first non-aqueous solvent preferably in combination with a co-solvent. Said co-solvent may include another first solvent of a type described therein. Preferably, however, it is of a different type. Said co-solvent is selected to affect the boiling point and/or dissolution properties of the solvent for the first material. The boiling point of said co-solvent may be less than 60° C., preferably less than 30° C., more preferably less than 15° C., especially less than 5° C. The boiling point of said co-solvent may be greater than −90° C., preferably greater than −70° C., more preferably greater than −50° C.

Preferably, said second solvent includes a major portion of said first solvent in combination with a minor portion of said co-solvent. Preferably, at least 90 wt %, more preferably at least 93 wt %, especially at least 97 wt % of said second solvent is comprised by said first non-aqueous solvent, especially by a hydrofluorocarbon solvent. The balance is preferably made up of one or more co-solvents as described.

Said co-solvent may be selected from hydrocarbons and ethers. Preferred hydrocarbons have up to six carbon atoms. They may be alicyclic or, preferably, aliphatic. They are preferably alkanes with methane, ethane, propane and butane being preferred. Preferred ethers are dialkylethers, for example, $C_1$ to $C_4$ dialkyl ethers, with dimethyl ether being especially preferred.

In the purification of the second compound using said second solvent, said second compound may be caused to precipitate, suitably by adjusting the pH as described above.

In the method of the first aspect, said catalytic conversion may result in the preparation of said second compound and a third compound. Said enzyme may be sensitive to the third compound, for example in the sense that relatively high concentrations of said third compound may reduce the ability of the enzyme to effect conversion. Where said first compound is of general formula $R^1NHQ$, said third compound may represent a compound of formula $R^iCOOH$ or a salt thereof. In this case, said second compound may represent a compound of formula $H_2NQ$ or a salt thereof. The method of the first aspect may include the step of separating the second and third compounds from one another. This may involve providing a solvent (which may be said first or second solvents described) in which said second and third compounds (or salts thereof) have different solubilities and/or have different partition coefficients and using this property to effect separation. The second and third compounds may be separated using a mixture comprising the solvent and water.

Said third compound, especially a free acid thereof, is preferably substantially soluble in the solvent used for the separation.

After isolation of said second compound it may be derivatised, suitably to produce an antibiotic.

Said first compound may be a natural penicillin, or a biosynthetic penicillin prepared by the addition of a precursor to penicillin fermentation broths, or a cephalosporin. Preferably said first compound is selected from Penicillin-G, Penicillin-X (p-hydroxyphenyl penicillin), Penicillin-V (phenoxymethyl penicillin) and cephalosporin G. Said second compound is preferably 6-aminopenicillanic acid or 7-aminodesacetoxycephalosporanic acid; and said third compound may be optionally substituted, especially unsubstituted, phenylacetic acid.

In one embodiment of the invention, penicillin acylase enzyme which has been immobilised on an insoluble matrix is charged to a jacketed reaction vessel followed by the required volume of water and penicillin-G is added whilst stirring. The reaction vessel is then sealed and vacuum is applied to achieve pressure of 10 mbar or less. The first solvent is charged to the reaction mixture. An aqueous solution of sodium hydroxide (range of 2.5–20% w/v or more) is introduced into the reaction to maintain a pH range of 7.0–9.0 especially about pH 8.0. The reaction temperature is maintained at approximately constant level throughout. A preferred temperature range is 20–50° C., more preferably 30–40° C.

At the end of the reaction, which is indicated by a constant pH reading without the need for further addition of aqueous NaOH solution, the reaction liquors are charged from the bottom of the reaction vessel into a second jacketed vessel (the evaporation vessel) via an in-line filter. The immobilised enzyme is thus recovered, washed with water and stored for further use.

The clear filtrate solution is cooled by flowing a coolant through the jacket. Preferred temperature is 0–20° C., more preferably 2–10° C. An aqueous solution of an inorganic acid, such as 1–4M nitric acid or 1–4M sulphuric acid is added slowly whilst stirring to a pH in the range of 3.5 to 4.0, with pH 3.8 being ideal. During this operation, the phenyl acetic acid (PAA) present as the sodium salt is converted to the free acid form which is soluble in the first solvent. Whilst the PAA is extracted into the first solvent, the 6-APA (in free acid form) is precipitated and is now present as a suspension. The reaction mixture may be stirred for a further 30 minutes to one hour whilst maintaining constant pH and temperature.

6-APA can be conveniently and simply isolated by charging the reaction mixture from the bottom of the evaporation vessel back to the reaction vessel via an in-line filter. Optionally, a filter element may be fitted to the bottom outlet of the vessel such as a wire mesh filter or a glass sinter.

According to a second aspect of the invention, there is provided a method of removing a third compound (preferably an acid or acid salt, especially PAA) as described herein from a mass of material containing the compound, the method comprising:

(a) contacting the mass of material with a solvent (for example said first solvent or especially said second solvent described herein) so as to charge the solvent with said third compound; and (b) separating charged solvent from the remainder of said mass of material.

Said third compound contacted in the method is preferably a free acid.

In the method, said third compound may be isolated by allowing the solvent to evaporate.

Any feature of any aspect of any invention or embodiment described herein may be combined with any feature of any aspect of any other invention or embodiment described herein.

DEFINITIONS

The following terms are used hereinafter:
Pen-G—refers to penicillin-G as shown in Scheme 1.
6-PAA—refers to 6-aminopenicillanic acid.
PAA—refers to phenylacetic acid.
MIBK—refers to methylisobutylketone.
Phytosol—refers to 1,1,1,2-tetrafluoroethane.
Phytosol D—refers to a mixture comprising dimethylether (10 wt %) and 1,1,1,2-tetrafluoroethane (90 wt %).

EXAMPLES

All analyses referred to hereinafter were carried out using HPLC as follows:
Mobile phase:25 mM ammonium acetate in 1:1 methanol/water solution+acetic acid to pH6.0.
Column:3.9×300 mm column, 10 micron C18 Reverse Phase packing.
Detection:230 nm
injection:10 μl
Example numbers prefixed with the letter "C" are comparative examples.

EXAMPLE C1

Standard (known) method for the preparation of 6-APA (i) Enzymatic De-Acylation of Pen-G Water (480 ml) and Penicillin-G (30 g) were charged into a beaker in a water bath set at 37° C. The mixture was stirred gently until the temperature was stabilised at 37° C. Enzyme resin (38 g) comprising penicillin acylase on a polymeric resin matrix was added followed by 5% NaOH to pH 8.0. Stirring was continued whilst maintaining pH 8.0 and 37° C. until a steady state was reached. This took about 2 hours. Total volume of 5% NaOH used was normally around 65 ml. The enzyme resin was filtered through a sintered funnel and the resin was washed with water and stored in a refrigerator for further use. The solution containing 6-APA and PAA was processed as described in (ii) below.

(ii) 6-APA Isolation

Enzymation liquor containing 6-APA and PAA was concentrated four-fold then chilled to 5° C. and an equal volume of MIBK was added. 2M nitric acid was added dropwise to pH 3.8. The pH was maintained at 3.8 for 1 hour, during which time, the free acid of 6-APA precipitated. Then, the precipitate was filtered, washed with MIBK, then acetone and dried.

EXAMPLE 1

General method according to embodiment of present invention

Methods (iii) and (iv) hereinafter are alternatives, both of which can be used for isolating 6-APA.

(i) Apparatus

An apparatus for carrying out the method comprises a reaction vessel a d an evaporation vessel, both of which are jacketed to provide a means for temperature control. In addition, both vessels are equipped with reagent addition burettes, and a means for stirring, measuring temperature and pH. Both vessels communicate with one another and with a vacuum pump and a gas compressor so that reaction streams can be transferred from one vessel to another and a volatile solvent used (as described herein) can be transferred into and from both vessels and a suitable solvent storage tank. In-line filters, one-way valves and pressure release valves may be fitted to allow convenient and safe operation of the apparatus.

(ii) Enzymatic De-acylation of Pen-G

Water (100 ml) and Pen-G (40 g) were charged to the reaction vessel followed by the enzyme resin (50.6 g). The vessel was sealed and evacuated to below 10 mbar pressure and agitation commenced. Phytosol A (1–2 Kg) was charged and the temperature was stabilised at 37° C. by flowing warm water through the jacket. A pH of 8.0 was maintained by the addition of 5% NaOH via the reagent burette until a steady state was reached. Total volume of NaOH solution required was normally around 90 ml.

(iii) 6-APA isolation

Enzymation liquor containing 6-APA and PAA was recharged to the reaction vessel. Phytosol D (1–2 Kg) was charged and agitation started. Cooling was applied by flowing cold water through the jacket. 2M nitric acid was slowly added via the reagent burette to pH 3.8 and stirring was continued for 1 hour whilst maintaining pH 3.8. During this time, the free acid of 6-APA precipitated, whilst the PAA remained in the solution in the Phytosol D.

The reaction mixture was charged to the evaporation vessel via an in-line filter which retained the 6-APA precipitate. Phytosol D was then re-circulated through the reaction vessel (to wash the 6-APA product) and the in-line filter for 30 minutes after which the Phytosol D flow was diverted back to the storage cylinder. The 6-APA precipitate was then isolated from the in-line filter. When all of the Phytosol D was evaporated, the remaining aqueous solution contained PAA as an oily suspension.

(iv) 6-APA isolation (alternative method)

The enzymatic liquor containing 6-APA and PAA was stirred with Phytosol A or Phytosol D or with an alternative solvent mix comprising 1, 1, 1, 2-tetrafluoroethane and a co-solvent of, for example, an aliphatic alcohol, ketone or ether. An inorganic acid, such as 1–4M nitric or sulphuric acid, was added slowly until a pH of less than 2.5 was reached. The pH is suitably adjusted to between 1.5 and 2.0. The temperature during the acid addition was reduced to within the range 2 to 20° C. The two immiscible layers were separated by allowing the mixture to settle and the lower layer comprising the PAA solution in solvent was run off. The upper layer containing 6-APA was treated with an aqueous solution of a base such as NaOH or KOH whilst stirring at a reduced temperature until pH 3.8 was reached at which pH the free acid of 6-APA precipitated. The precipitated 6-APA was isolated by filtration.

(v) PAA isolation

The aqueous solution comprising the oily suspension of PAA produced in step (iii) was extracted into Phytosol solvent and the immiscible Phytosol layer containing PAA in solution was separated from the aqueous layer. Isolation of the PAA was achieved by causing the Phytosol to evaporate. Alternatively, PAA can be isolated after step (iv) by evaporating the solvent from the isolated PAA solution.

EXAMPLE C2

Preparation of 6-APA

The method of Example C1 was carried out to produce a baseline for comparison with other examples. In the method Pen-G (30 g) was reacted with the immobilised enzyme and the final product (6-APA) was dried, weighed and assayed using HPLC.

Results were as follows:

| | |
|---|---|
| Weight Pen-G used | =30.0 g |
| Weight immobilised enzyme | =38.0 g |
| Volume of water used | =480 ml |
| Volume 5% NaOH used | =65 ml |
| Volume of enzymation liquor produced | =550 ml |
| Assay of enzymation liquor | =31,100 µg/ml as 6-APA |
| Conversion Step yield | =96% |
| Weight 6-APA produced | =13.23 g |
| Overall yield from Pen-G | =74% |

EXAMPLE 2

A slurry was prepared in the reaction vessel containing Pen-G (40 g), water (50 ml) and Phytosol (2 Kg). 5% NaOH was added over 2 hours during which time the pH was maintained at 8.0. The total volume of NaOH solution used was 85 ml, indicating full conversion. At the end of the reaction, the enzyme resin was filtered off and the Phytosol was evaporated back to its storage tank.

Volume of enzymation liquor=160 ml

Assay of enzymation liquor=142, 300 µg/ml

Weight 6-APA produced=22.76 g

Conversion yield=98.2%

80 ml of the enzymation liquor was precipitated and 6-APA was isolated following the method described in Example 1 (iii).

Weight 6-APA produced=9.6 g

Overall yield from Pen-G=84.4%

The product obtained was dry and no further vacuum drying was necessary.

EXAMPLE C3

To provide a direct comparison with the 6-APA isolation step of Example 2, a second 80 ml portion of the enzymation liquor was precipitated using MIBK, washed with acetone and dried under vacuum for 20 hours.

Weight of 6-APA produced=9.45 g

Isolation step yield=83.0%.

EXAMPLE 3

Effect of pH on extraction of PAA

This example was carried out to assess the efficiency and selectivity of Phytosol D in extracting PAA from the enzymatic liquor at different pH's.

The enzymatic liquor was prepared as described in Example 1 using the enzyme resin from Example C2.

20 ml samples of the liquor were extracted with 40 ml of Phytosol D, at various pH's, using hand held apparatus as follows:

The apparatus consists of a 100 ml graduated glass tube fitted with a filter assembly and a clamping ring which in turn is fitted with a needle valve. The material or solution to be extracted is charged into the tube. The filter is then assembled with the aid of a sealing O ring followed by the clamping ring ensuring that a tight fit is achieved. Phytosol liquid gas is introduced to the glass tube from an aerosol can via the needle valve. The contents of the tube are mixed by vigorous shaking after which the tube is inverted and allowed to stand until the two layers are separated. The Phytosol is then released via the needle valve into an evaporator bottle taking care not to allow any of the aqueous layer to co-discharge. Results are provided in the table below.

| pH | 6-APA Removed (% of total w/w) | PAA Removed (% of total w/w) |
|---|---|---|
| 8.0 | 0 | 0 |
| 6.5 | 0 | <2 |
| 5.3 | 0 | 6.5 |
| 3.8 | <1 | >99 |
| 1.4 | <1 | >99 |

EXAMPLE 4

Effect of Phytosol A presence on enzymation yield

The experiment was carried out to assess the effect of Phytosol A presence on enzymation yield—that is, (6-APA produced in enzymation)—(theoretical 6-APA). In the experiment, Pen-G (30 g) was dissolved in water (300 ml) and de-acylated as described in Example 1.

| | |
|---|---|
| Volume of 2.5% NaOH used | =134 ml |
| Volume enzymation liquor produced | =450 ml |
| Assay or enzymation liquor | =38,120 µg/ml as 6-APA |
| Enzymation yield | =98.2% of theoretical |

It will be noted that the yield is greater in the presence of Phytosol A (compare Example 4 and Example C2).

EXAMPLE 5

Effect of using more concentrated solution of Pen-G

This experiment involved the conversion of a more concentrated solution of Pen-G, with a view to avoiding the need for further concentration prior to the 6-APA precipitation and isolation step of Example 1 (iii). In the experiment, Pen-G (30 g) was dissolved in water (150 ml) and Phytosol A (2 Kg) was used and the method carried out as described above.

| | |
|---|---|
| Final volume or enzymation liquor | =350 ml |
| Assay of enzymation liquor | =47,800 µg/ml as 6-APA |
| Conversion yield | =96% |

6-APA was isolated as described in Example 1 (iii) by adding the enzymation liquor to Phytosol D (2 Kg) and acidifying to pH 3.8 using 1M nitric acid.

Weight of 6-APA product isolated=5.6 g

It will be appreciated that the concentration of the enzymatic liquor used is preferably as high as possible to minimise losses of the desired 6-APA in the mother liquor.

EXAMPLE 6

Isolation of PAA

A previously obtained aqueous effluent solution (300 ml) containing PAA (14 g approximately) as an oil suspension was charged to the reaction vessel. Phytosol D was charged to the vessel and the mixture stirred for 30 minutes. The two layers were allowed to settle by standing for 15 minutes then separated with the aid of a sight glass fitted to the bottom outlet of the vessel. The Phytosol D was then evaporated and returned back to the storage cylinder. PAA was collected from the vessel as an off-white crystalline solid.

| | |
|---|---|
| Weight of PAA recovered | =14.2 g |

Although it is difficult to accurately determine the PAA content of the starting solution, yields close to the theoretical appear to be possible.

EXAMPLE 7

Use of sulphuric acid for pH adjustment

The enzymation reaction was carried out as described generally in Example 1 (ii) using Pen-G (40 g), enzyme resin (61 g), water (50 ml), 5% NaOH to maintain pH 8.0 and at a temperature of 37° C.

Results were as follows:

| Enzymation liquor volume | =145 ml |
|---|---|
| Concentration | =13.2% (by HPLC) |
| Enzymation step yield | =83% |

The precipitation and isolation was carried out as described generally in Example 1 (iii), using a solvent mixture comprising Phytosol (2 kg) and iso-propanol (30 ml). 6-APA was caused to precipitate by adding 1M sulphuric acid to pH 3.8 at 4° C.

6-APA was isolated as a white solid

| Weight yield | =14.8 g |
|---|---|

HPLC analysis showed PAA as a very small trace.

Preferred embodiments of the present invention may have the following advantages:

- the enzymation reaction can be carried out on a solution with higher concentration of Pen-G than hitherto, thereby eliminating or reducing the need for a potentially costly concentration step.
- a more efficient enzyme reaction is achieved involving a faster reaction and/or improved yield. Conversion yields of 98% or higher have been demonstrated.
- the activity of the enzyme is not damaged by said solvent system.
- the need for large amounts of organic solvents is eliminated or reduced, thereby eliminating problems associated with such solvents such as storage, recovery and effluent treatment prior to disposal.
- Phytosol shows good efficiency in removing PAA whilst the solubility of 6-APA in the solvent is negligible.
- Chrystal forms can be manipulated by the use of a co-solvent during precipitation of 6-APA which may be advantageous in downstream processing.
- Dry 6-APA is produced directly, without the need for further product drying.
- Overall, the process is faster and cheaper than the established industrial processes.

Advantageously, the present invention in its broadest terms is not restricted to penicillin and cephalosporin splitting enzymes but is relevant to other related enzymes including acylases, amidases, proteases and esterases. The solvents described herein may be used to substantially enhance reaction rates and streamline product isolation.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

What is claimed is:

1. A method of preparing a second compound by enzymatic catalytic conversion of a first compound, the method comprising contacting said first compound and an enzyme in a first solvent mixture comprising water and a first non-aqueous solvent, wherein said first non-aqueous solvent is a fluorinated, non-chlorinated alkane, alkene or alkyne having up to four carbon atoms, and allowing said enzyme to convert said first compound to said second compound.

2. A method according to claim 1, wherein said enzyme is sensitive to said second compound in that relatively high concentrations of said second compound reduce the ability of the enzyme to effect the conversion.

3. A method according to claim 1, wherein said enzyme is capable of catalyzing a de-acylation reaction.

4. A method according to claim 1, wherein said first compound is of general formula $R^1NHQ$ wherein $R^1$ is a functional group selected from the group consisting of unsubstituted and substituted alkylcarbonyl groups and Q is a functional group selected from the group consisting of unsubstituted and substituted cyclic groups.

5. A method according to claim 1, wherein the ratio of the weight of said first solvent to that of water is said solvent mixture is at least 2.

6. A method according to claim 1, wherein the ratio, as % w/v, of said first compound to the water present in said mixture is at least 10.

7. A method according to claim 1, wherein said first non-aqueous solvent has a boiling point, at atmospheric pressure, of less than 80° C. and greater than −90° C.

8. A method according to claim 1, wherein said first solvent is tetrafluoroethane.

9. A method according to claim 1, including the step of precipitating the second compound from said first solvent mixture and subsequently isolating the precipitate.

10. A method according to claim 1, wherein said first compound is a natural penicillin or a bio-synthetic penicillin prepared by the addition of a precursor to a penicillin fermentation broth, or a cephalosporin and said second compound is 6-amino penicillanic acid or 7-aminodesacetoxycephalosporanic acid.

11. A method according to claim 1 wherein said enzymatic catalytic conversion results in the preparation of said second compound and a third compound wherein said first compound is of general formula $R^1NHQ$ wherein $R^1$ is a functional group selected from the group consisting of unsubstituted and substituted alkylcarbonyl groups and Q is a functional group selected from the group consisting of unsubstituted and substituted cyclic groups, and said third compound is of formula $R^1COOH$ or a salt thereof and the method includes separating the second and third compounds from one another.

12. A method according to claim 1, the method including contacting the first solvent mixture with a second non-aqueous solvent thereby to form a second solvent mixture having a first phase and a second phase immiscible therewith, and adjusting the pH of the second solvent mixture to a value at which the second compound is substantially soluble in the first phase and at least one by-product of the enzymatic catalytic conversion is substantially soluble in the second phase immiscible with said first phase.

13. A method according to claim 1, wherein the first non-aqueous solvent has a boiling point, at atmospheric pressure, less than 20° C.

14. A method according to claim 1, wherein the first non-aqueous solvent is 1,1,1,2-tetrafluoroethane.

15. A method according to claim 1, wherein the ratio of the first compound to water in the solvent mixture is at least 50% (w/v).

16. A method according to claim 1, wherein the ratio of the weight of the first non-aqueous solvent to that of water in the solvent mixture is at least 10.

17. A method according to claim 12, wherein the second solvent is 1,1,1,2-tetrafluoroethane.

18. A method according to claim 1, the method including a step of separating the second compound from a third compound also prepared by the enzymatic catalytic conversion of the first compound.

19. A method according to claim 18, wherein said separating step comprises:
   a) contacting a mixture comprising the second and third compounds with said first non-aqueous solvent so as to dissolve said third compound in the first non-aqueous solvent; and
   b) separating a second non-aqueous solvent, comprising said first non-aqueous solvent that contains said third compound, from the mixture.

20. A method according to claim 18, wherein the third compound is a free acid.

21. A method according to claim 19, wherein the first non-aqueous solvent is 1,1,1,2-tetrafluoroethane.

22. A method as claimed in claim 1, wherein the first non-aqueous solvent is a non-chlorinated, fluorinated $C_{1-4}$ alkane.

23. A method according to claim 18, wherein said separating step comprises:
   a) contacting a mixture comprising the second and third compounds with a second non-aqueous solvent comprising said first non-aqueous solvent in combination with a co-solvent so as to dissolve said third compound in the second non-aqueous solvent; and
   b) separating the second non-aqueous solvent, comprising said first non-aqueous solvent in combination with a co-solvent that contains said third compound, from the mixture.

* * * * *